(12) United States Patent
Timko et al.

(10) Patent No.: US 12,351,606 B2
(45) Date of Patent: *Jul. 8, 2025

(54) COMPOSITIONS AND RELATED METHODS FOR MODULATING TRANSCRIPTIONAL ACTIVATION BY INCORPORATING GAG MOTIFS UPSTREAM OF CORE PROMOTER ELEMENTS

(71) Applicant: UNIVERSITY OF VIRGINIA PATENT FOUNDATION, Charlottesville, VA (US)

(72) Inventors: Michael Paul Timko, Charlottesville, VA (US); Paul J. Rushton, Brookings, SD (US); Marta Tatiana Bokowiec, Charlottesville, VA (US)

(73) Assignee: University Of Virginia Patent Foundation, Charlottesville, VA (US)

( * ) Notice: Subject to any disclaimer, the term of this patent is extended or adjusted under 35 U.S.C. 154(b) by 677 days.

This patent is subject to a terminal disclaimer.

(21) Appl. No.: 16/725,065

(22) Filed: Dec. 23, 2019

(65) Prior Publication Data

US 2020/0123211 A1 Apr. 23, 2020

Related U.S. Application Data

(60) Division of application No. 15/618,578, filed on Jun. 9, 2017, now Pat. No. 10,550,162, which is a continuation of application No. 14/658,529, filed on Mar. 16, 2015, now Pat. No. 9,677,083, which is a continuation of application No. 12/676,867, filed as application No. PCT/US2008/010446 on Sep. 5, 2008, now Pat. No. 8,980,633.

(60) Provisional application No. 60/935,947, filed on Sep. 7, 2007, provisional application No. 60/935,948, filed on Sep. 7, 2007.

(51) Int. Cl.
*C07K 14/415* (2006.01)
*C12N 15/82* (2006.01)

(52) U.S. Cl.
CPC ........ *C07K 14/415* (2013.01); *C12N 15/8243* (2013.01)

(58) Field of Classification Search
None
See application file for complete search history.

(56) References Cited

U.S. PATENT DOCUMENTS

| | | | |
|---|---|---|---|
| 4,459,355 A | 7/1984 | Cello et al. | |
| 4,795,855 A | 1/1989 | Fillatti et al. | |
| 4,940,838 A | 7/1990 | Schiulperoort et al. | |
| 4,945,050 A | 7/1990 | Sanford et al. | |
| 5,015,580 A | 5/1991 | Christou et al. | |
| 8,980,633 B2* | 3/2015 | Timko | C12N 15/8243 435/468 |
| 9,677,083 B2* | 6/2017 | Timko | C12N 15/8243 |
| 10,550,162 B2* | 2/2020 | Timko | C12N 15/8243 |
| 2004/0029167 A1* | 2/2004 | Fritig | C12N 15/8283 435/320.1 |
| 2011/0173721 A1 | 7/2011 | Albino et al. | |

FOREIGN PATENT DOCUMENTS

| | | |
|---|---|---|
| WO | WO 00/67558 A1 | 11/2000 |
| WO | WO 2000/67558 | * 11/2000 |
| WO | WO 00/67558 B1 | 2/2001 |

OTHER PUBLICATIONS

Xu et al 2004 (Plant Molecular Biology 55: p. 743-761) (Year: 2004).*
Riechers et al., "Structure and expression of the gene family encoding putrescine N-methyltransferase in *Nicotiana tabacum*: new clues to the evolutionary origin of cultivated tobacco," *Plant Molecular Biology*, 41:387-401 (1999).
Sachan et al., "Wound-induced gene expression of putrescine N-methyltransferase in leaves of *Nicotiana tabacum*," *Phytochemistry*, 61:797-805 (2002).
SCORE Search Results for Albino et al., U.S. Appl. No. 15/618,578, pp. 1-11 (2007).
SCORE Search Results for Timko, International Publication No. WO 00/67558, pp. 1-10 (2015).
Shoji et al., "Jasmonate Induction of Putrescine N-Methyltransferase Genes in the Root of *Nicotiana sylvestris*," *Plant Cell Physiol.*, 41(7):831-839 (2000).
Xu et al., "Methyl jasmonate induced expression of the tobacco putrescine N-Methyltransferase genes requires both G-box and GCC-motif elements," *Plant Molecular Biology*, 55:743-761 (2004).
Facchini, "Alkaloid Biosynthesis in Plants: Biochemistry, Cell Biology, Molecular Regulation, and Metabolic Engineering Applications," *Annu. Rev. Plant Physiol. Plant Mol. Biol* 52, pp. 29-66 (2001) (electronic publication).
International Search Report dated Nov. 10, 2009 issued in International Application No. PCT/US2008/010446.
Katoh et al., "Molecular biology of pyridine nucleotide and nicotine biosynthesis," *Frontiers in Bioscience*, 9, pp. 1577/1586 (May/Jun. 2004) (Irvine, California, US).
Oksman-Caldentey, "Tropane and Nicotine Alkaloid Biosynthesis-Novel Approaches Towards Biotechnological Production of Plant-Derived Pharmaceuticals," *Current Pharmaceutical Biotechnology*, 8, pp. 203-210 (Sep. 2007) (Potomac, Maryland, US).

* cited by examiner

Primary Examiner — Matthew R Keogh
(74) Attorney, Agent, or Firm — Arnold & Porter Kaye Scholer LLP

(57) ABSTRACT

Compositions and methods for genetically modifying the production levels of nicotine and other alkaloids in plants are provided.

9 Claims, 11 Drawing Sheets
Specification includes a Sequence Listing.

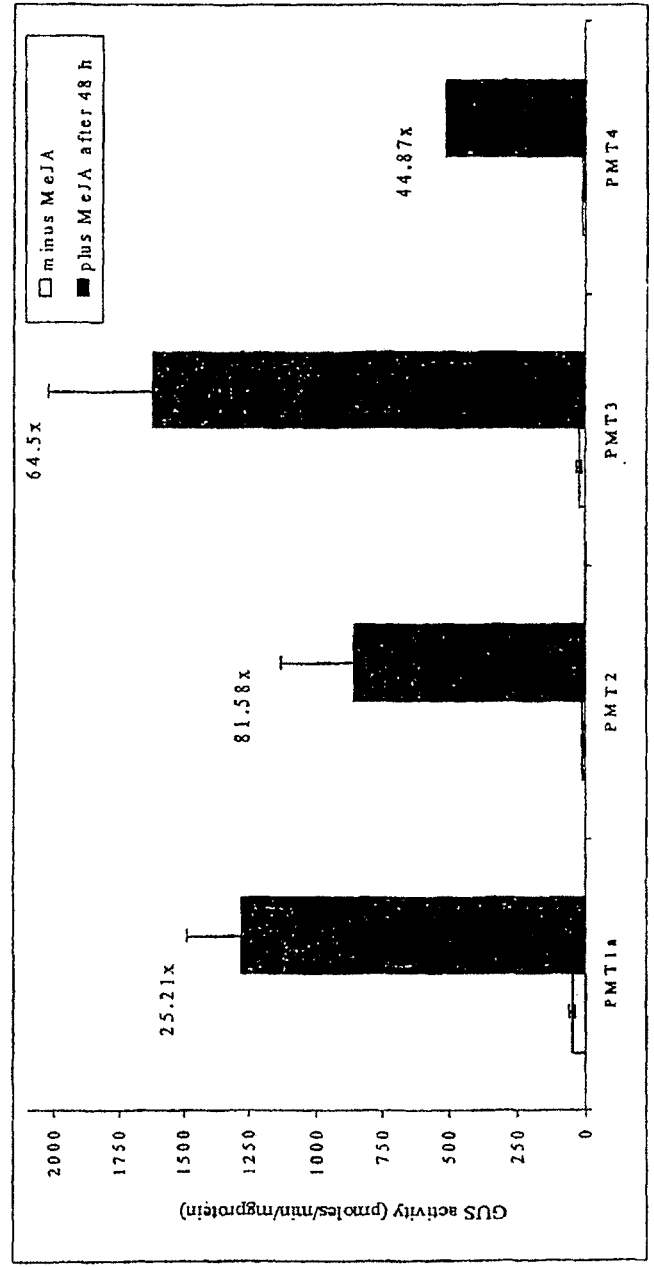

COMPOSITIONS AND RELATED METHODS FOR MODULATING TRANSCRIPTIONAL ACTIVATION BY INCORPORATING GAG MOTIFS UPSTREAM OF CORE PROMOTER ELEMENTS

CROSS-REFERENCE TO RELATED APPLICATIONS AND INCORPORATION OF SEQUENCE LISTING

This application is a divisional of U.S. patent application Ser. No. 15/618,578, filed Jun. 9, 2017, which is a continuation of U.S. patent application Ser. No. 14/658,529, filed Mar. 16, 2015 now U.S. Pat. No. 9,677,083, issued Jun. 13, 2017), which is a continuation of U.S. patent application Ser. No. 12/676,867, filed Oct. 28, 2010 (now U.S. Pat. No. 8,980,633, issued Mar. 17, 2015), which is a U.S. National Stage of PCT/US2008/010446, filed Sep. 5, 2008, which claims the benefit of U.S. Provisional Application No. 60/935,948, filed Sep. 7, 2007, and U.S. Provisional Application No. 60/935,947, filed Sep. 7, 2007, all of which are incorporated by reference in their entireties herein. A sequence listing contained in the file named "P34712US03_SL.TXT" which is 5,208 bytes (measured in MS-Windows®) and created on Dec. 23, 2019, is filed electronically herewith and incorporated by reference in its entirety.

BACKGROUND

Nicotine production from polyamine putrescine, a precursor of nicotine, can be produced by two pathways in plants. Putrescine can be synthesized directly from ornithine in a reaction catalyzed by the enzyme ornithine decarboxylase, or can be produced indirectly from arginine in a sequence of reactions initiated by arginine decarboxylase. The first committed step in nicotine biosynthesis is the conversion of putrescine to N-methylputrescine by putrescine N-methyltransferase ("PMT"). N-methylputrescine is subsequently oxidized by a diamine oxidase, and is cyclized to produce a 1-methyl-$\Delta^1$-pyrrolium cation, which is subsequently condensed with nicotinic acid to produce nicotine.

SUMMARY

In various embodiments, compositions and methods for genetically modifying the production levels of nicotine and other alkaloids in plants are provided. Nicotine and other alkaloid production can be genetically controlled by modulating the transcriptional activation of various genes that encode gene products involved in the biosynthetic pathway of such alkaloids. Various compositions and methods for genetically modifying the production levels of nicotine in plants, including the tobacco, are provided. The transcriptional activation of a promoter of interest can be modified by incorporating one or more GAG motifs upstream and operably-linked to the promoter of interest in order to control the gene expression levels of a transgene of interest, which can be positioned downstream and operably-linked to the promoter of interest. Various compositions and improved methods for genetically regulating the production levels of nicotine and other alkaloids in plants, including transgenic plants, transgenic tobacco plants, recombinant stable cell lines, recombinant stable tobacco cell lines, and derivatives thereof, are provided.

In one embodiment, an expression vector for regulating expression of a plant gene is provided, the vector comprising a tripartite GAG motif having at least 95% nucleotide sequence identity to the nucleotide sequence of SEQ ID NO:1, where the tripartite regulatory-motif comprises a G-box like element, an AT-rich element and a GCC-like box element and where the expression of an operatively-linked gene is capable of being induced by a phytohormone.

In another embodiment, an expression vector for regulating expression of a plant gene is provided, the vector comprising a G-G derivative fragment having at least 95% nucleotide sequence identity to the nucleotide sequence of SEQ ID NO:5, where the regulatory-motif comprises a G-box like element, and a GCC-like box element and where the expression of an operatively-linked gene is induced by a phytohormone.

In a further embodiment, the expression vector may contain multiple copies of the tripartite GAG motif or G-G derivative fragment. For example, the regulatory motif may be present in the expression vector as a dimer, a trimer or a tetramer.

In yet another embodiment, a method for regulating synthesis of a protein in a plant is provided, the method comprising introducing into the plant cell an expression vector comprising a tripartite GAG motif into a plant cell where the GAG motif comprises a G-box like element, an AT-rich element and a GCC-like box element, and the motif is capable of altering the induction of expression of a gene operatively-linked to the GAG motif.

BRIEF DESCRIPTION OF DRAWINGS

FIG. 2A illustrates the nucleotide sequence of the NtPMT1a gene promoter from −201 to +67, relative to the transcription initiation site (+1). The GAG motif is indicated by an arrow and the G Box-like element, the AT-rich element, and the GCC-like element are shown as boxed subregions. Numbers indicate the position relative to the transcription initiation site. FIG. 2B is a schematic representation of the gain-of-function promoter constructs. Tetramers (4×GAG) were inserted upstream of the −46 35S promoter of the Cauliflower mosaic virus (CaMV 35S). Promoter activity was monitored by GUS reporter gene activation.

FIG. 3A is a schematic representation of the GAG motif and mutated GAG motif constructs. The G Box-like element is represented by a circle, the AT-rich element by an oval, and the GCC-like element by a rectangle. Mutated versions are represented as shaded regions. FIG. 3B shows the relative strengths and methyl jasmonate inducibility of various promoter constructs. Black bars represent the level of GUS activity 48 hours after the addition of 100 µM MeJA. Grey bars represent the level of GUS activity after 48 hours in control samples. The relative fold inducibility of respective promoter constructs is shown. Error bars indicate plus and minus the standard error of the mean (SEM).

FIG. 4A is a schematic representation of various GAG motif constructs, each containing individual elements or combinations of elements. The G Box-like element is represented by a circle, the AT-rich element by an oval, and the GCC-like element by a rectangle. The G Box construct comprises a tetramer (4×) of the G Box-like element; the AT-rich region construct comprises a tetramer (4×) of the AT-rich element; the GCC Box construct comprises a tetramer (4×) of the GCC-like element; the G Box-GCC Box construct comprises a tetramer (4×) of the G Box-like element and the GCC-like element; and the GAG fragment construct comprises a tetramer (4×) of the GAG motif (G Box-like element, AT-rich element, and GCC-like element). FIG. 4B shows the relative strengths and methyl jasmonate inducibility of the promoter constructs. Black bars represent the level of GUS activity 48 hours after the addition of 100 μM MeJA. Grey bars represent the level of GUS activity after 48 hours in control samples. The relative fold inducibility of respective promoter constructs is shown. Error bars indicate plus and minus the standard error of the mean (SEM).

FIG. 5A is a schematic representation of the G box-GCC unit construct and the mutated "G box-GCC unit" construct. The G Box-like element is represented by a circle. The GCC-like element is represented by a rectangle. Mutated versions are shaded. FIG. 5B shows the relative strengths and methyl jasmonate inducibility of the promoter constructs. Black bars represent the level of GUS activity 48 hours after the addition of 100 μM MeJA. Grey bars represent the level of GUS activity after 48 hours in control samples. The relative fold inducibility of respective promoter constructs is shown. Error bars indicate plus and minus the standard error of the mean (SEM).

FIGS. 6A-6B illustrate the functional domains of GAG motifs derived from four N. tabacum PMT genes. FIG. 6A shows a comparative sequence alignment of the GAG motifs derived from the NtPMT1a, NtPMT2, NtPMT3, and NtPMT4 genes. The G box element, the AT-rich element, and the GCC-like element have been underscored. Stars indicate positions of variant sequences. FIG. 6B shows the relative strengths and methyl jasmonate inducibility of the GAG motifs from four PMT genes of Nicotiana tabacum. Black bars represent the level of GUS activity 48 hours after the addition of 100 μM MeJA. Grey bars represent the level of GUS activity after 48 hours in control samples. The relative fold inducibility of respective promoter constructs is shown. Error bars indicate plus and minus the standard error of the mean (SEM).

DETAILED DESCRIPTION

Figure 1:
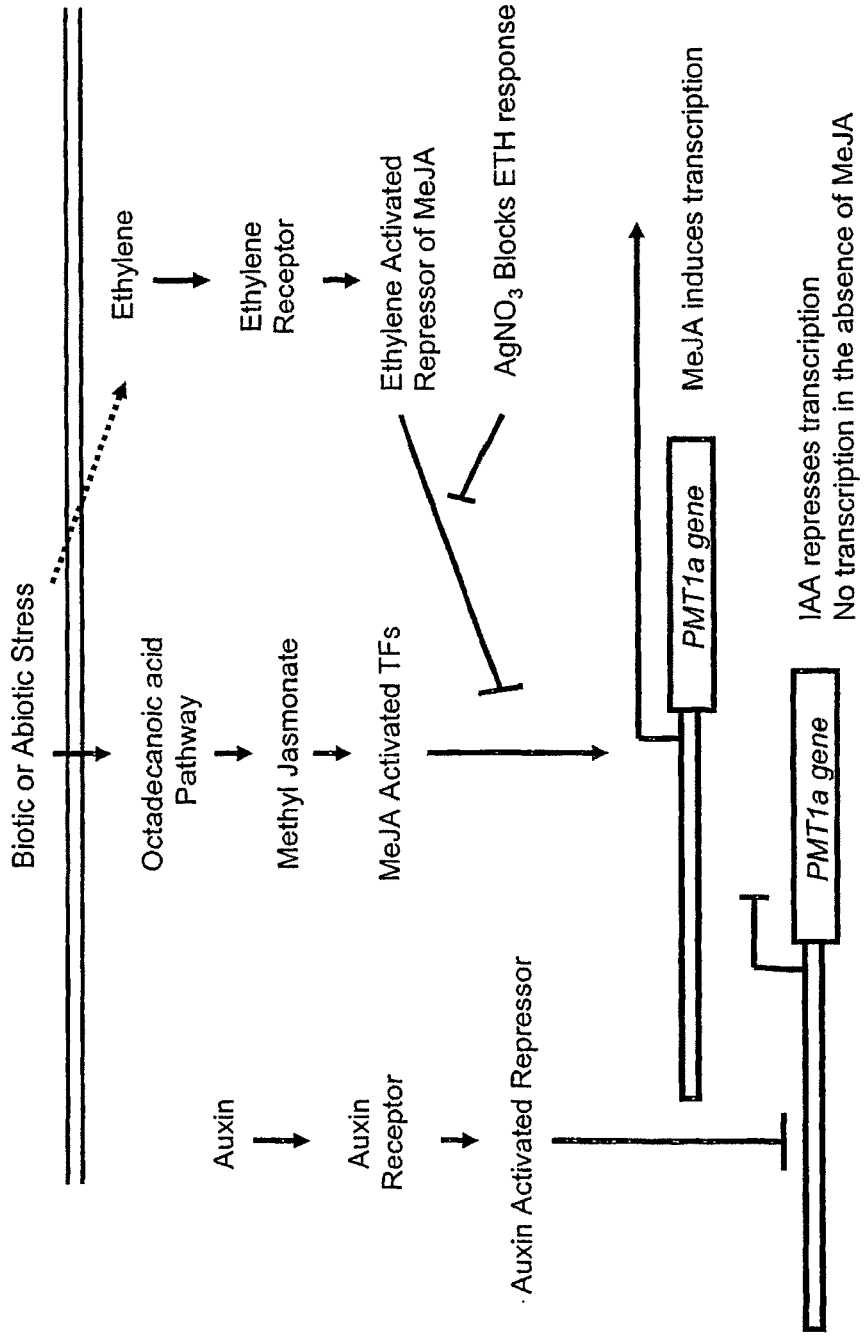
FIG. 1 illustrates multiple signal transduction pathways, induced by various stimuli that regulate PMT promoter activation/repression in plants.

Genetic regulation of nicotine biosynthesis is desirable in a variety of plants, especially in tobacco plants. Nicotine biosynthesis can be regulated by controlling the expression levels and/or the activities of enzymes involved in the nicotine biosynthetic pathway. In particular, an effective way to genetically regulate nicotine production is by controlling the transcriptional activation of promoters that control the expression of genes encoding putrescine N-methyltransferases ("PMT"). PMT is one of several critical enzymes involved in the nicotine biosynthetic pathway in plants, including tobacco plants. Various compositions and methods for modifying PMT expression levels in plants are provided, as further described below. In Nicotiana tabacum, at least five PMT genes have been characterized: NtPMT1a, NtPMT1b, NtPMT2, NtPMT3, and NtPMT4.

For example, the production levels of nicotine, other alkaloids, and secondary metabolites can be genetically regulated by controlling the expression level of PMT, which correlates directly with their production levels. This can be accomplished by controlling PMT promoter activation that correlates with the expression levels of the PMT structural gene. PMT RNA transcripts produced by transcriptional processes are subsequently translated into PMT polypeptides that exhibit PMT enzymatic activity. The activation of the PMT promoter by sequence-specific transcriptional factors ("transcriptional activators") can increase the levels of PMT RNA transcripts and PMT polypeptides produced. In contrast, the repression of the PMT promoter by sequence-specific transcriptional factors ("transcriptional repressors") can decrease the levels of PMT RNA transcripts and PMT polypeptides produced.

The disclosure describes the characterization of a regulatory region identified from sequences located upstream of the core promoter elements of the PMT1A promoter. This regulatory region is referred to as the "GAG motif," which comprises a G-box like element [G], an AT-rich element [A], and a GCC-like box element [G].

The GAG motif, having the sequence (CTAACCCTGCACG TTGTAATGAATTTTTAACTATTATATTATATCGAGTTGCGCCCTCCACTC CTCGGTGTCCA), is designated as SEQ ID NO:1. The G-box like element [G], having the sequence (GCACGTTG), is designated as SEQ ID NO:2. The AT-rich element [A], having the sequence (TAATGAATTTTTAACTA TTATATTATAT), is designated as SEQ ID NO: 3. The GCC-like box element [G], having the sequence (TGCGCC CTCCACTCCTCGGTGTCCA), is designated as SEQ ID NO:4. The G-G derivative fragment, having the sequence (CTAACCCTGCACGTTGTCGAGTTGCGCCCTC-CACTCCTCGG TGTCCA), is designated as SEQ ID NO:5. The G-box like element [G], the AT-rich element [A], and the GCC-like box element [G] included in the GAG motif, as disclosed herein, have not been previously characterized, and the sequences are different from other G-box elements, AT-rich elements, and GCC elements, previously reported in the literature.

Experimental results, described herein, have shown that when individual components of the GAG motif (i.e., the G-box like element [G], the AT-rich element [A], and the GCC-like box element [G]) are positioned upstream and operably-linked to test promoters, the levels of promoter activation for promoter constructs containing such individual elements of the GAG motif, in intact form, are substantially lower than that observed when the GAG motif is positioned upstream and operably-linked to the same test promoters. Thus, as an intact tripartite unit, the GAG motif can function optimally when positioned upstream and operably-linked to various homologous and heterologous promoters of interest. In this context, the term "homologous promoters" refer to PMT promoters or PMT-like promoters. In this context, the term "heterologous promoters" refer to promoters distinct from PMT promoters or PMT-like promoters.

Single or multiple copies of the GAG motif and GAG derivative fragments, including the G-G derivative fragment, can be incorporated upstream and operably-linked to a promoter of interest, which is positioned upstream and operably-linked to a transgene of interest. The terms "operably-linked" and "operably associated" are used interchangeably herein to broadly refer to a chemical or physical coupling (directly or indirectly) of two otherwise distinct domains in a molecule, wherein each domain has independent biological function. For example, operably-linked refers to the functional connection between a regulatory sequence and the polynucleotide regulated by the regulatory sequence. For example, an operably-linked GAG motif of the disclosure can comprise a GAG motif operably-linked to a promoter, which is in turn operably-linked to a polynucleotide encoding a polypeptide or inhibitory nucleic acid molecule.

A "promoter" is a regulatory sequence composed of a region of a DNA molecule, typically within 100 nucleotides upstream of the point at which transcription starts (generally near the initiation site for RNA polymerase II). Promoters are involved in recognition and binding of RNA polymerase and other proteins to initiate and modulate transcription. To bring a coding sequence under the control of a promoter, it typically is necessary to position the translation initiation site of the translational reading frame of the polypeptide between one and about fifty nucleotides downstream of the promoter.

A "minimal promoter" comprises only a necessary amount of sequence for assembly of a transcription complex required for transcription initiation. Minimal promoters typically include a "TATA box" element that may be located between about 15 and about 35 nucleotides upstream from the site of transcription initiation. Minimal promoters may also include a "CCAAT box" element (typically the sequence CCAAT) and/or a GGGCG sequence, which can be located between about 40 and about 200 nucleotides, typically about 60 to about 120 nucleotides, upstream from the transcription start site.

Incorporation of multiple copies of the GAG motif upstream of a promoter of interest can increase the strength of the promoter of interest, and thereby, result in higher expression levels of the transgene of interest. To enhance promoter activation, for example, one or more GAG-fragments can be positioned upstream of a minimal plant promoter containing a TATA box for recruiting RNA Polymerase, and preferably, in close proximity to the 5' end of the TATA box. A "plant promoter" is a promoter capable of initiating transcription in plant cells. Such promoters need not be of plant origin. For example, promoters derived from plant viruses, such as the CaMV 35S promoter, or from *Agrobacterium tumefaciens* such as the T-DNA promoters, can serve as plant promoters. An example of a plant promoter of plant origin is the maize ubiquitin-1 (ubi-1) promoter. The GAG motif can be used in conjunction with any promoter (native or synthetic, minimal or complete) that can be operative in plants (i.e., recognized by plant cellular factors). Suitable promoters include the −46 bp Cauliflower Mosaic Virus (CaMV) 35S minimal promoter, which can be expressed at low (basal) levels in most plant tissues. Tissue-specific promoters, such root-specific promoters or root cortex specific promoters, are also contemplated. Suitable promoters include constitutive promoters and inducible promoters, well-known to persons skilled in the art. Suitable promoters and methods for constructing various promoter constructs are well-known by persons skilled in the art.

PMT promoter activation is responsive to various endogenous and exogenous signals, including phytohormones, wounding, and invasion by pathogens or insects. FIG. 1 illustrates the existence of multiple signal transduction pathways inducible by various phytohormones, including jasmonic acid ("JA"), auxin, and ethylene, which can affect PMT promoter activation. As shown in FIG. 1, the transcriptional regulation of PMT genes can be responsive to multiple signal transduction pathways that can be co-induced if multiple stimulants exist simultaneously in an environment. When a particular signal transduction pathway is induced, the expression level and/or the transcriptional activity of a transcriptional factor can be increased. Alternatively, the expression level and/or the transcriptional activity of a transcriptional factor can be decreased by inducing a particular signal transduction pathway. For example, a JA-inducible signal transduction pathway can be blocked by co-exposure to sufficient concentrations of auxin and/or ethylene that appear to have antagonistic effects on the JA-inducible pathway. In particular, PMT promoter activation induced by JA exposure can be blocked by exposure to auxin and/or ethylene.

The GAG motif and derivatives of the GAG motif can modulate the expression levels of a transgene of interest in a tissue-specific manner. For example, the PMT gene expression in the roots of *N. tabacum* can be up-regulated by various stresses/stimuli, including topping procedures, physical invasions by herbivores/insects, and methyl jasmonate (MeJA) exposure. Thus, the incorporation of one or more GAG motifs and/or derivatives of the GAG motifs, including partial configurations and variants of the GAG motif (e.g., G-G fragment) can be utilized to activate any promoter of interest in a root-specific manner, and in response to various stresses/stimuli.

For modulating the activation levels of various promoters of interest and/or expression levels of various transgenes of interest, the following compositions and methods are contemplated:

For various expression vectors described below, various genes that encode enzymes involved in biosynthetic pathways for the production of alkaloids, flavoids, and nicotine can be suitable as transgenes that can be operably-linked to a promoter of interest.

In another embodiment, an expression vector comprises a promoter operably-linked to cDNA encoding an enzyme involved in the biosynthesis of alkaloids. In another embodiment, a plant cell line comprises an expression vector comprising a promoter operably-linked to cDNA encoding an enzyme involved in the biosynthesis of alkaloids. In another embodiment, a transgenic plant comprises an expression vector comprising a promoter operably-linked to cDNA encoding an enzyme involved in the biosynthesis of alkaloids. In another embodiment, methods for modulating the production level of alkaloids are provided, comprising: introducing an expression vector comprising a promoter operably-linked to cDNA encoding an enzyme involved in the biosynthesis of alkaloids.

In another embodiment, an expression vector comprises a promoter operably-linked to cDNA encoding an enzyme involved in the biosynthesis of flavoids. In another embodiment, a plant cell line comprises an expression vector comprising a promoter operably-linked to cDNA encoding an enzyme involved in the biosynthesis of flavoids. In another embodiment, a transgenic plant comprises an expression vector comprising a promoter operably-linked to cDNA encoding an enzyme involved in the biosynthesis of flavoids. In another embodiment, methods for modulating the production level of flavoids are provided, comprising: introducing an expression vector comprising a promoter operably-linked to cDNA encoding an enzyme involved in the biosynthesis of flavoids.

In another embodiment, an expression vector comprises a promoter operably-linked to cDNA encoding an enzyme involved in nicotine biosynthesis. In another embodiment, a plant cell line comprises an expression vector comprising a promoter operably-linked to cDNA encoding an enzyme involved in nicotine biosynthesis. In another embodiment, a transgenic plant comprises an expression vector comprising a promoter operably-linked to cDNA encoding an enzyme involved in nicotine biosynthesis. In a preferred embodiment, the enzyme is PMT involved in nicotine biosynthesis. In another embodiment, methods for modulating the production level of nicotine are provided, comprising: introducing an expression vector comprising a promoter operably-linked to cDNA encoding an enzyme involved in nicotine biosynthesis.

Various embodiments are directed to expression constructs comprising at least one GAG motif (SEQ ID NO:1), and subfragments thereof; and/or at least one derivative GAG motif (SEQ ID NO:5), and subfragments thereof. Expression constructs further comprise suitable minimal core plant promoter, a transgene of interest, an upstream (5') regulatory region, a downstream (3') regulatory region, including transcription termination and polyadenylation signals, and other sequences required for efficient and specific expression known to persons skilled in the art.

Various embodiments are directed to transgenic plants, including plants of the genus *Nicotiana*, various species of *Nicotiana*, including *N. tabacum*, *N. rustica* and *N. glutinosa*, and related members of the genus *Solanaceae*. Suitable plants for transformation include any strain or variety of tobacco, any plant tissue capable of transformation by various methods of transforming plants known by persons skilled in the art, including U.S. Pat. No. 4,459,355 that discloses a method for transforming susceptible plants, including dicots, with an *Agrobacterium* strain containing the Ti plasmid; U.S. Pat. No. 4,795,855 that discloses transformation of woody plants with an *Agrobacterium* vector; U.S. Pat. No. 4,940,838 that discloses a binary *Agrobacterium* vector; U.S. Pat. Nos. 4,945,050; and 5,015,580.

Various embodiments are directed to methods for reducing/increasing expression levels of a transgene of interest in a plant cell, comprising an expression construct comprising at least one GAG motif (SEQ ID NO:1), and fragments thereof; and derivative GAG motif (SEQ ID NO:5) and fragments thereof.

Various embodiments are directed to methods for increasing expression of a transgene in a plant cell specifically in response to phytohormone inducibility (e.g., response to jasmonic acid and methyl jasmonate), comprising: an expression construct comprising at least one GAG motif (SEQ ID NO:1), and fragments thereof; and derivative GAG motif (SEQ ID NO:5) and fragments thereof.

Transgenic tobacco plants containing the disclosed expression vectors can produce altered levels of alkaloids, flavoids, and nicotine. The tobacco leaves of such transgenic tobacco plants can be utilized for producing various tobacco products, including the manufacture of pipes, cigars, and cigarettes, and chewing tobacco, and may be produced in any form, including leaf tobacco, shredded tobacco, or cut tobacco. Altered nicotine content can improve resistance to insects.

Various embodiments are directed to seeds derived from genetically-modified transgenic plants described herein.

Various embodiments are directed to various polynucleotide molecules that can suppress the expression levels of genes involved in the biosynthetic pathways for the production of alkaloids, flavoids, and nicotine. Examples of suitable compositions include ERF and Myc anti-sense polynucleotides that are complementary to ERF and Myc transcript sequences, such as RNAi molecules, microRNAs, and other dominant negative constructs known to persons skilled in the art.

EXAMPLES

Growth of Plant Cell Cultures

Tobacco (*N. tabacum* L.) Bright Yellow-2 (BY-2) cell suspension cultures were grown in Murashige-Skoog (MS) medium containing 3% (w/v) sucrose and 0.2 mg/l 2,4-dichlorophenyoxyacetic acid (2,4-D), pH 5.8, essentially as described by An (1985). Cell suspensions were subcultured in fresh MS medium every 7 days.

Construction of Synthetic Promoters

Promoter constructs were produced by annealing phosphorylated upper- and lower-strand oligonucleotides to create various elements containing a SpeI restriction site at the 5' end and an XbaI restriction site at the 3' end. These were introduced into MS23-β-glucuronidase ("GUS") between the SpeI and XbaI sites.

Promoter constructs containing multiple copies of elements or combinations of elements in any desired order were obtained by digesting the constructs with either SpeI or XbaI together with SacI, which cuts the plasmid at boundaries of a synthetic promoter of interest. Ligation of two such fragments can recreate the plasmid with multiple copies of an element of interest. This can be repeated, as the 5' SpeI and the 3' XbaI sites are recreated, but internal SpeI-XbaI ligations result in the loss of these restriction sites. For analysis in *N. tabacum*, the entire synthetic promoter was excised as a HindIII-SacI fragment and ligated into the binary vector pGPTV-GUS-KAN.

Transformation of Bright Yellow-2 Cells

Ten colonies of transformed Agrobacteria (*A. tumefaciens*) containing the promoter construct were picked from a fresh plate and inoculated into 10 ml YEB, containing 50 mg/l rifampicin and 50 mg/l kanamycin, in a 50 ml flask. Cell cultures were incubated overnight at 28° C. with shaking, an overnight culture (1 ml) was taken. Cultures were diluted with YEB plus antibiotics so that the $OD_{600}$ was approximately 0.3. Agrobacteria were grown at 28° C. with shaking until the $OD_{600}$ was about 0.6. Cells were pelleted by centrifugation. Supernatants were removed and agrobacteria were resuspended in 0.5 ml MS. Approximately 3 ml of wild type BY-2 cells were introduced into Petri dishes. Approximately 100 µl of undiluted Agrobacteria or 1:10 or 1:100 diluted agrobacteria were mixed with the BY-2 cells to infect them. After 2 days, the BY-2 cells were washed with 30 ml MS medium and left for 30 min before the supernatant was removed. Approximately 2 ml aliquots of the transformed BY-2 cells were deposited onto MS plates containing vitamins, 50 mg/l kanamycin, and 500 mg/l cefotaxin. Transformed calli were visible after 3-5 weeks.

Culturing and Treating of BY-2 Cells with Methyl Jasmonate

Single transformed calli were picked from selection plates and put on fresh MS+agar plates containing vitamins, 50 mg/l kanamycin, and 500 mg/l cefotaxin. Additionally, small amounts of calli were deposited into micro-wells (Corning 6 well culture cluster) with 6 ml MS medium containing vitamins, kanamycin, and cefotaxin. Samples in the micro-wells were grown at 28° C. for 4 days with shaking. Approximately 1 ml cells from the micro-wells were sub-cultured to new micro-wells with 5 ml fresh MS medium with vitamins, 50 mg/l kanamycin, and 500 mg/l cefotaxin. BY-2 cells were grown at 28° C. for 3 days with shaking. Then ten independent lines were chosen and 0.4 ml cells from each of the liquid cultures were subcultured to a 250 ml Erlenmeyer flask with 45 ml MS medium, vitamins, 50 mg/l kanamycin, and 500 mg/l cefotaxin. Cells were grown at 28° C. for 2 days with shaking. Then 10 ml cells from each flask were introduced into new 250 ml Erlenmeyer flasks with 40 ml MS medium containing vitamins without hormones (−2.4D) and antibiotics. The BY-2 cells were grown at 28° C. for 1 day with shaking. After 1 day BY-2 cells were treated with different amounts of methyl jasmonate (MeJA).

Determination of GUS Reporter Activity

Histochemical staining for GUS activity and GUS activity determination was performed as described by Jefferson (1987).

Transformation, Culture, and Treatment of Tobacco Plants with MeJA

Ten colonies of the transformed Agrobacteria containing a promoter construct of interest were picked from a fresh plate and inoculated into 10 ml YEB, containing 50 mg/l rifampicin, and 50 mg/l kanamycin, in a 50 ml flask. Cell cultures were incubated overnight at 28° C. with shaking. Approximately 1 ml of overnight culture was taken. Cultures were diluted with 50 ml YEB plus antibiotics so that the $OD_{600}$ was approximately 0.3. Agrobacteria were grown at 28° C. with shaking until the $OD_{600}$ was approximately 0.6. The cells were then pelleted by centrifugation. Supernatants were removed and Agrobacteria were resuspended in 40 ml fresh YEB by pipetting with a 1 ml tip. Wild type tobacco leaves were cut into small pieces under sterile conditions and put in a 50 ml beaker. Agrobacteria solution was poured onto the tobacco leaves and the mixture was swirled together and left for 5 min for the Agrobacteria to infect the leaves. Infected leaves were put on MS plates with filter paper (to limit Agrobacteria grow). The MS plates did not contain antibiotics. Plates were left for 2 days in the dark. After 2 days the tobacco pieces were transferred onto MS plates containing 1 mg/l 6 BA, 500 mg/l cefotaxin and 100 mg/l kanamycin. Samples were left in the light at 28° C. After 1 month small transgenic tobacco plants were visible. The plants were transferred to pots with ½ MS medium with 150 mg/l kanamycin. Several week old plants were transplanted into soil and grown under standard greenhouse conditions. Seeds from primary transformants were collected and germinated on ½ MS medium with 150 mg/l kanamycin and 500 mg/l cefotaxin. Transgenic seedlings were tested for promoter activity.

Testing Promoter Activity in Transgenic Tobacco Plants

Second generation transgenic tobacco plants containing various promoter::GUS constructs were used to test promoters for activity and wound inducibility or jasmonate inducibility. Three-week old transgenic plants were transferred to sterile pots containing 180 ml ½ MS, and were suspended by plastic so that the roots were submerged in the medium but the aerial parts of the plants were in the air. The plants were grown for two weeks before exposure to 25 µM MeJA or being subjected to wounding of aerial parts or roots by squashing with serrated tweezers. After 72 hours, the plants were stained for GUS activity.

Mutational Analysis of Individual Elements of NtPMT1a GAG Motif

Figure 2A:
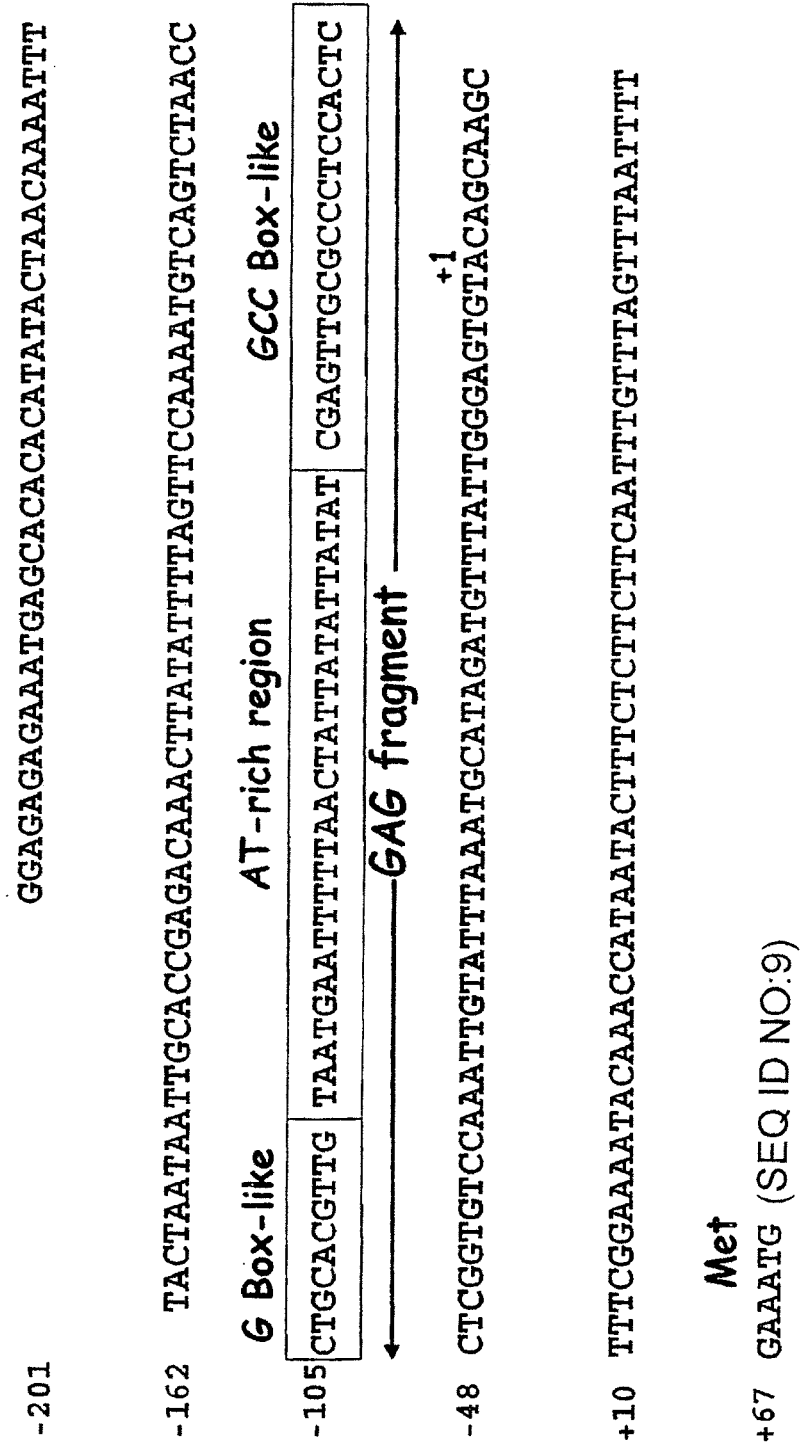
FIGS. 2A-2B illustrate a promoter sequence containing the GAG motif that confers methyl jasmonate (MeJA) inducible expression of the tobacco NtPMT1a gene.
Figure 2B:
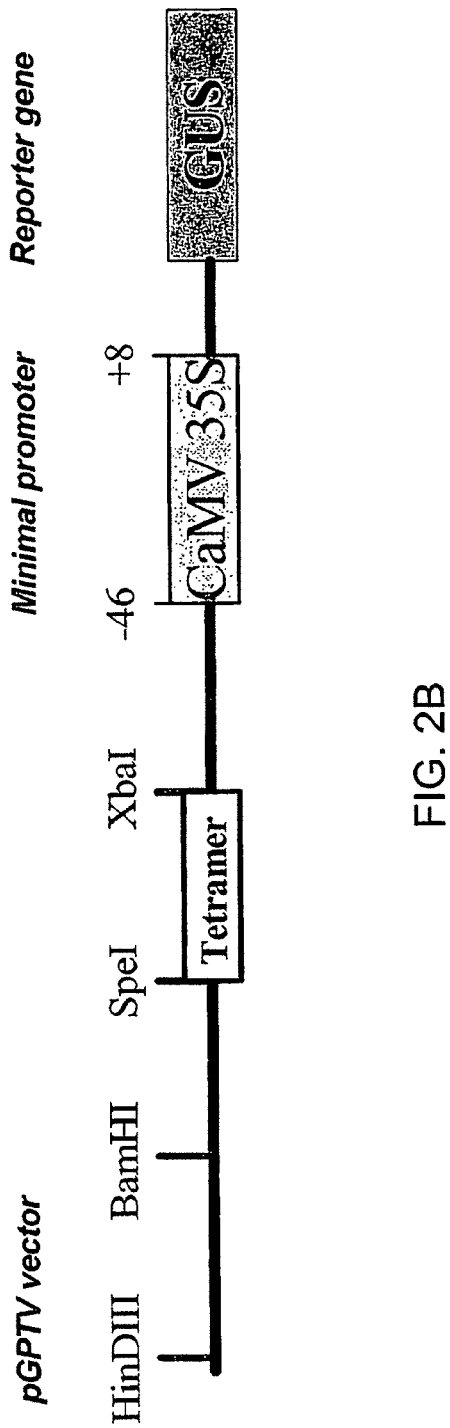

Previous experiments designed to investigate the nature and location of regulatory elements that control NtPMT1a gene expression showed that a minimal fragment of 111 bp, isolated upstream of the transcriptional start site, was sufficient to confer MeJA-responsiveness. More extensive mutagenesis studies indicated the existence of at least three functionally distinguishable elements: a G Box-like element at −103 to −96, an AT-rich region at −80 to −69, and a GCC-like element located at −62 to −56. This region containing all three elements is referred to as the GAG motif, or the GAG motif (FIG. 2A). Further analysis established which elements are required for jasmonate inducibility, and which elements are sufficient to direct jasmonate inducibility. By taking a gain-of-function approach, various promoter constructs, tetramers of the GAG motif, placed upstream of the CaMV-46 minimal promoter, which was placed upstream of a GUS reporter gene were incorporated into the binary vector pGPTV (FIG. 2B). Each of the three elements within the GAG motif was mutated to determine the contribution of each element to both promoter strength and inducibility (FIG. 3A).

An improved method for the analysis of promoter activity in BY-2 cells was developed. Transformed BY-2 calli were grown on selection plates and subsequently grown as liquid cultures in MS medium. For each individual construct ten independent lines were chosen. Approximately 0.5 ml cells from each of the liquid cultures were subcultured together in MS medium that contain vitamins, kanamycin, and cefotaxin. After 2 days, the cells were diluted in fresh MS medium containing vitamins without hormones (−2.4D) to reduce any stress response induced by cell density, and to deplete the medium of auxin. It has been shown previously that high auxin levels in the medium decreased the extent of MeJA-induced NtPMT:GUS expression (Xu and Timko, 2004). After 1 day BY-2 cells were treated with 100 µM MeJA. After 48 hours cell samples were taken, and were used to determine the GUS activity. For statistical analysis, each experiment was repeated four times and to avoid day to day variation in the GUS activities, and the data were normalized. These cell culture conditions ensured both a rapid and uniform response to MeJA.

Figure 3A:
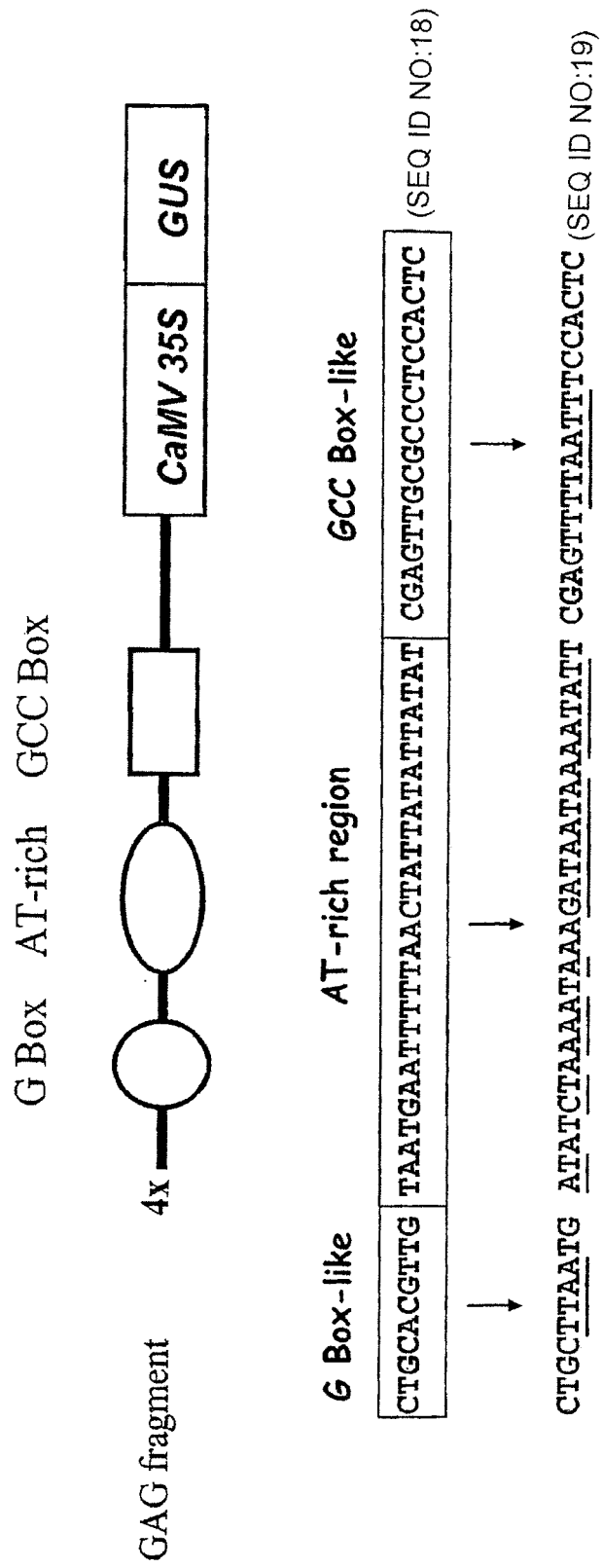
FIGS. 3A-3B illustrate the functional domains of the GAG motif as determined by mutational analysis.

To better characterize the GAG motif, a number of different constructs were made, and were tested in gain-of-function experiments by placing four copies of each element in front of the minimal CaMV 35S-46 promoter (FIG. 3A). Four tetramer constructs were tested: a GAG motif; a GAG motif containing a mutated G Box-like element in which the core sequence of ACGT in the G box was mutated to TTAA; a GAG motif containing a mutated GCC-like box in which the GCGCCC sequence in the GCC-like box was mutated to TTAATT; and a GAG motif containing a mutated AT-rich region consisting of the same number of A and T residues as the native GAG motif but in a different order.

Figure 3B:
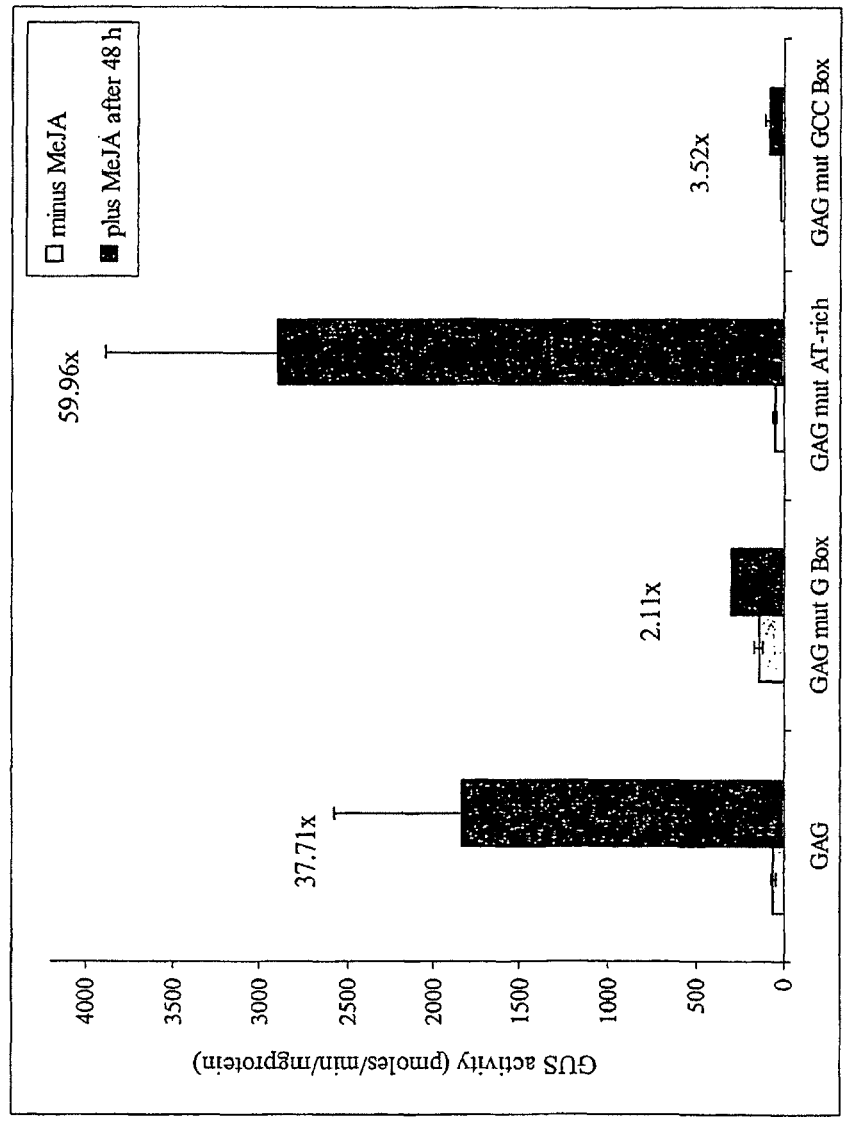

FIG. 3B shows clearly that a tetramer of the GAG motif can direct high level MeJA-induced expression (approximately 35-fold inducibility). FIG. 3B also shows that the mutation in the AT-rich region has insubstantial effect on the response of the GAG motif after MeJA treatment. However, the other mutations have a strong effect on the response of the tested fragment after MeJA treatment. Mutations of either the G Box-like element, or the GCC-like box, can abolish MeJA-induced expression. FIG. 3B also shows that a tetramer of the GAG motif with mutated G Box-like element has a higher background in the absence of MeJA than the GAG motif itself. In the absence of MeJA, the G Box-like element can act as a negative element. Alternatively, in the presence of MeJA, the G Box-like element can act as a positive element.

Figure 4A:
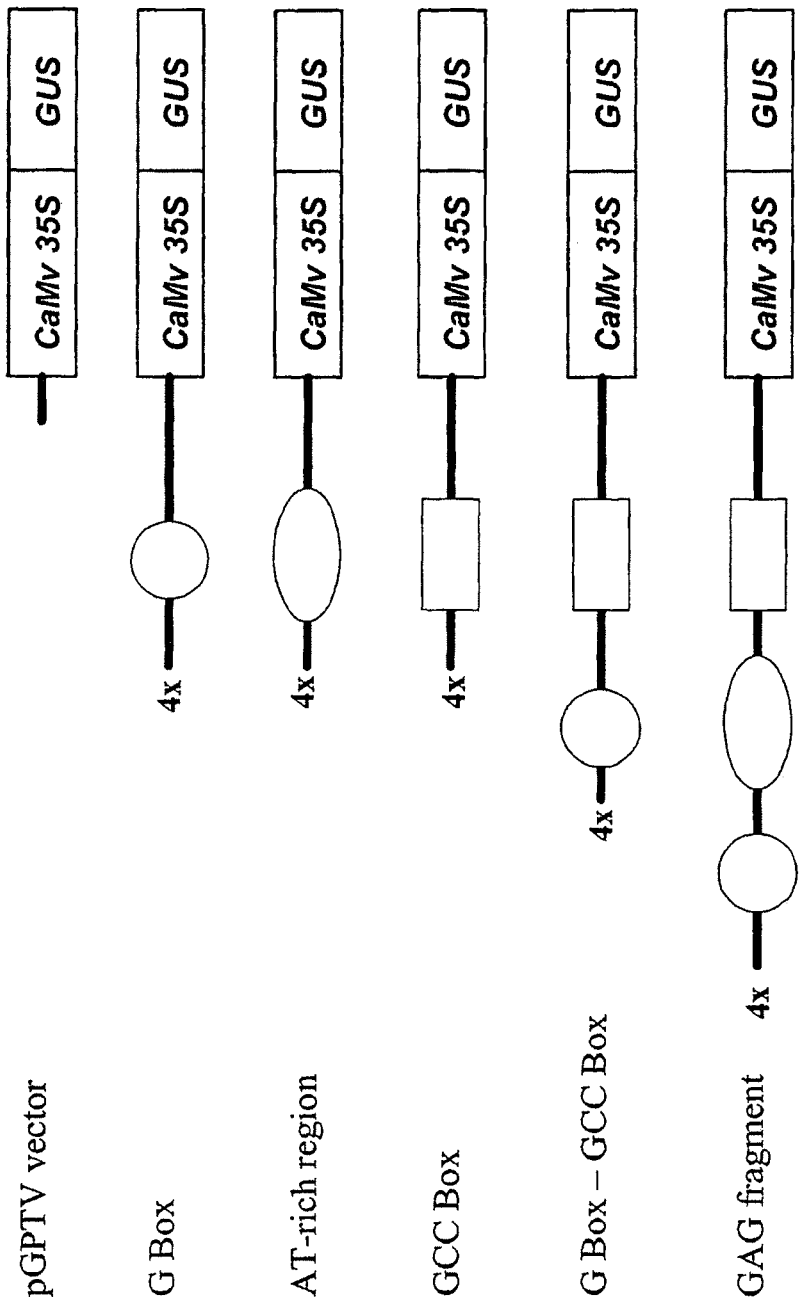
FIGS. 4A-4B illustrate the functional domains of the GAG motif as determined by assaying individual subfragments of the GAG motif.
Figure 4B:
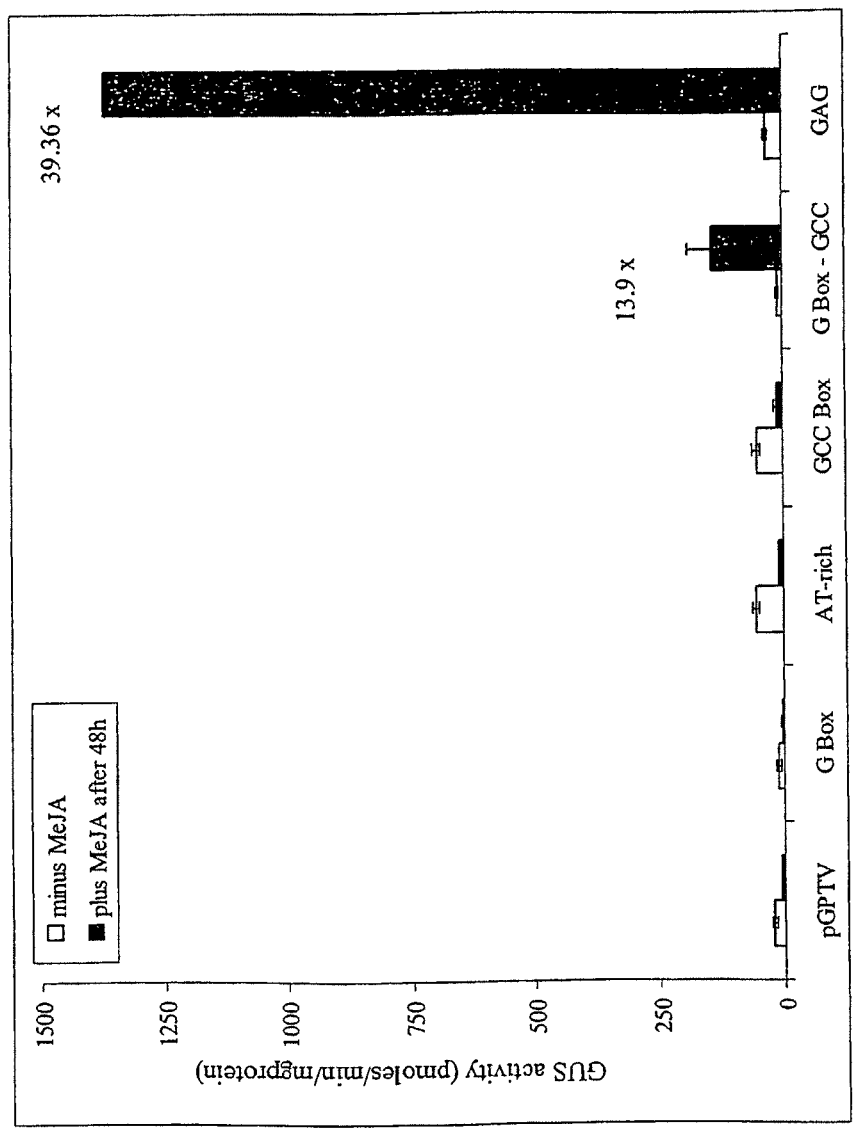

Gain-of-Function Experiments with the Individual Elements in the NtPMT1a GAG Motif FIG. 3 illustrates that both, the G Box-like element and the GCC-like box element, are necessary for MeJA-inducible expression in BY-2 cells. Gain-of-function experiments were conducted to determine which elements, or combinations of elements, are sufficient to direct MeJA-inducible expression. For these experiments, tetramers of individual elements, or combinations of elements, were inserted in front of the minimal CaMV 35S-46 promoter (FIG. 4A). Ten independent BY-2 cell lines carrying each construct were tested for promoter strength and inducibility by MeJA. FIG. 4B shows that the pGPTV vector showed only low level promoter activity with a characteristic reduction after MeJA treatment. A tetramer of the G Box-like element showed very similar results to that obtained by testing the vector control deficient in the tetramer. Low promoter activity and the characteristic reduction after MeJA exposure were observed, suggesting that the G Box-like element alone is insufficient is supporting promoter activation in BY-2 cells. FIG. 4A also shows the promoter activity of a tetramer of the AT-rich element with and without the addition of 100 µM MeJA. The AT-rich element showed only low level promoter activity and a characteristic reduction in promoter activity after MeJA addition. Comparison with the results obtained by testing the vector control, pGPTV, suggested that this reduction in activity is a feature of the expression vector and not characteristic of the AT-rich region. Similar to the results observed for the G Box element and the AT-rich element, a tetramer of the GCC-like box showed only low level promoter activity, and the level of GUS activity showed the characteristic reduction in every line tested after MeJA addition. These data clearly show that none of the elements of the GAG motif is sufficient to support full promoter activation. However, FIG. 4B also shows that the results obtained with a tetramer of the combination (the G Box-like element and the GCC-like box element) are significantly different from the results obtained by individually testing the individual elements in isolation from the other native elements of the GAG motif. The results showed that the G Box-GCC combination (deficient in the AT-rich element) can be induced by MeJA (approximately 10-15 fold inducibility). Furthermore, neither, the G Box nor the GCC-like Box element, individually, is sufficient to support promoter activation in BY-2 cells. Both, the G Box and the GCC-like Box elements, is responsive to MeJA, thus demonstrating that the G Box and the GCC-like element form a functional unit.

To determine how strong and how inducible the tetramer of the G Box-GCC is compared to the tetramer of the complete GAG motif, these two constructs were tested at the same time (FIG. 4B). The result show that the tetramer of the GAG motif is much stronger than the G Box-GCC element, and that the deletion of the AT-rich region greatly reduces promoter strength. The MeJA-inducibility of the GAG motif and the G Box-GCC are relatively similar, and that the elements responsible for MeJA induction of the GAG motif are probably present in the G Box-GCC portions of the GAG motif.

Analysis of the G Box-GCC Unit

Figure 5A:
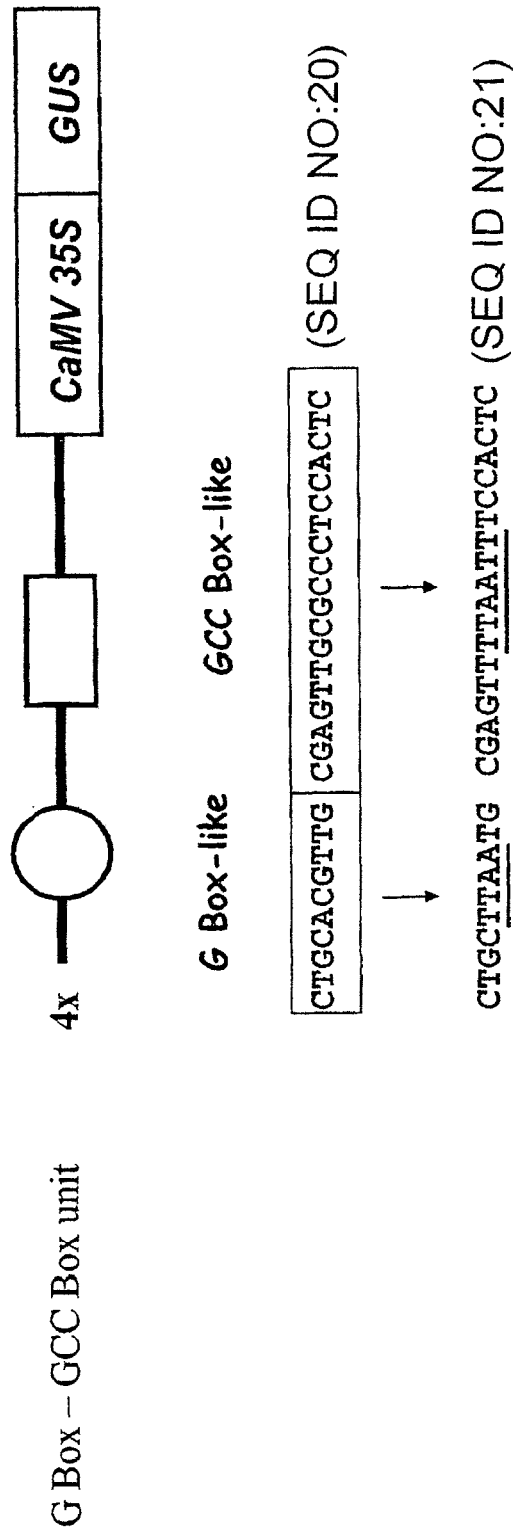
FIGS. 5A-5B illustrate the functional domains of the GAG motif deficient in the AT-rich element ("G box-GCC unit") as determined by mutational analysis.
Figure 5B:
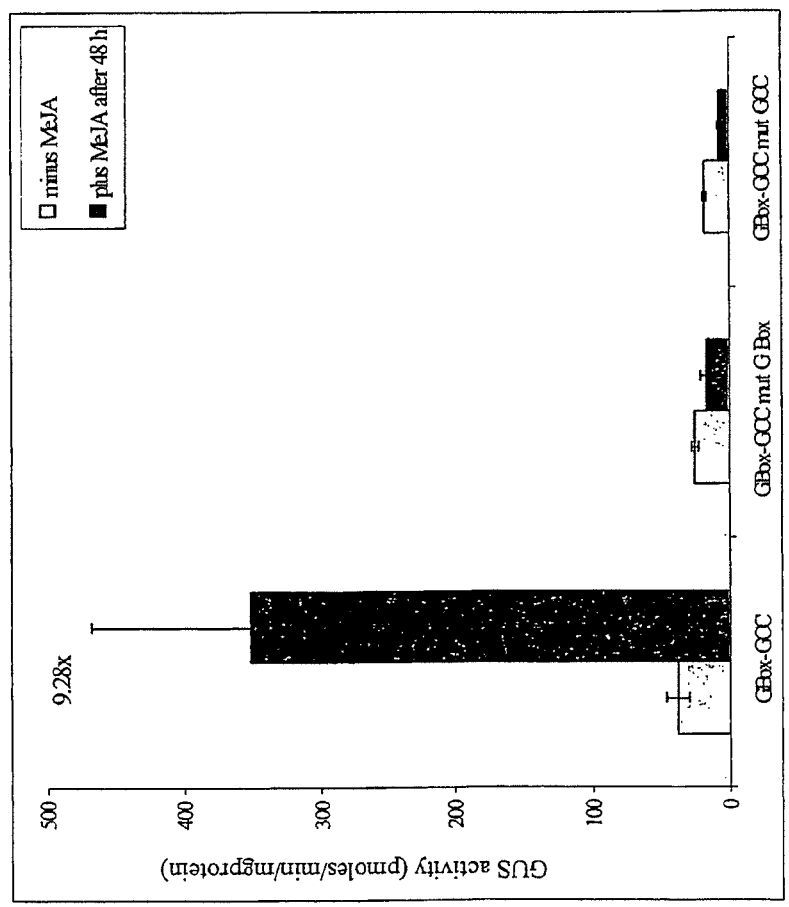

The G Box-GCC unit (29 bp) is shown to be sufficient for directing approximately 10-fold inducibility by MeJA. To further analyze this composite 29 bp unit, mutations were introduced into either the G Box-like or the GCC-like element. The core sequence of ACGT in the G box was mutated to TTAA, and the GCGCCC sequence in the GCC-like box was mutated to TTAATT (FIG. 5A). These mutations were the same as those introduced into the GAG motif. FIG. 5B shows that either mutations of the G Box-like element, or the GCC-like box element, totally abolished MeJA-inducible expression. This shows that the "G Box-GCC unit," although consisting of 29 nucleotides in length, contains two functionally distinguishable elements, and that both elements are necessary for MeJA-inducible expression.

Comparative Analysis of GAG Motifs of Different Tobacco PMT Gene Promoters

In tobacco, five different PMT genes have been identified: NtPMT1a, NtPMT1b, NtPMT2, NtPMT3 and NtPMT4. The expression kinetics and levels of transcript accumulation differs for each of the five N. tabacum PMT gene family members. These five genes also respond differently to phytohormones such as MeJA, ethylene and auxin. A comparison of four of the different PMT genes, NtPMT1a, NtPMT2, NtPMT3, and NtPMT4 have showed that all four genes are clearly inducible by MeJA. An inspection of the promoter regions of all four genes have shown that they all contain the GAG motif (approximately 111 bp) upstream of the transcriptional start site. Minor differences can be distinguished within these GAG motifs (FIG. 6A). Given the functional significance of the GCC-like box (FIGS. 5A and 5B), the most critical domain may be identified by evaluating differences in the sequences within the GCC-box in the NtPMT3 gene promoter (CGAGTT<u>C</u>CGCCCTCCACTC) and the GCC-boxes from other PMT gene promoters (CGAGTT<u>G</u>CGCCCTCCACTC). The other major variation is a difference in the length of the AT-rich region. This region is 3 bp longer in the GAG motif from the NtPMT1a gene promoter compared to the GAG motifs from the other three genes. One bp difference is also present within the G Box-like element (in which the sequence is CTG<u>C</u>ACGTTG in NtPMT1a), and the three other PMT genes have the sequence ATG<u>C</u>ACGTTG.

To test whether the differences in nucleotide sequence have any effect on the promoter strength or inducibility, and to determine whether the GAG motif from all four PMT genes are responsible for MeJA-inducibility, tetramers of all four GAG motifs were tested in gain-of-function experiments.

FIG. 6B shows, that despite minor sequence differences, all four GAG motifs can activate the promoter at similar levels, and can direct high level MeJA-inducible expression (approximately 25-80-fold inducibility). This suggests that the 1 bp difference in either, the G Box-like element or the GCC-like box element, does not have an effect on MeJA-inducible expression, and also that the 3 bp difference in the length of the AT-rich element does not change the nature of this element. Taken together, the results suggest that the GAG motifs can direct MeJA-inducible expression of all tobacco PMT genes.

Figure 7:
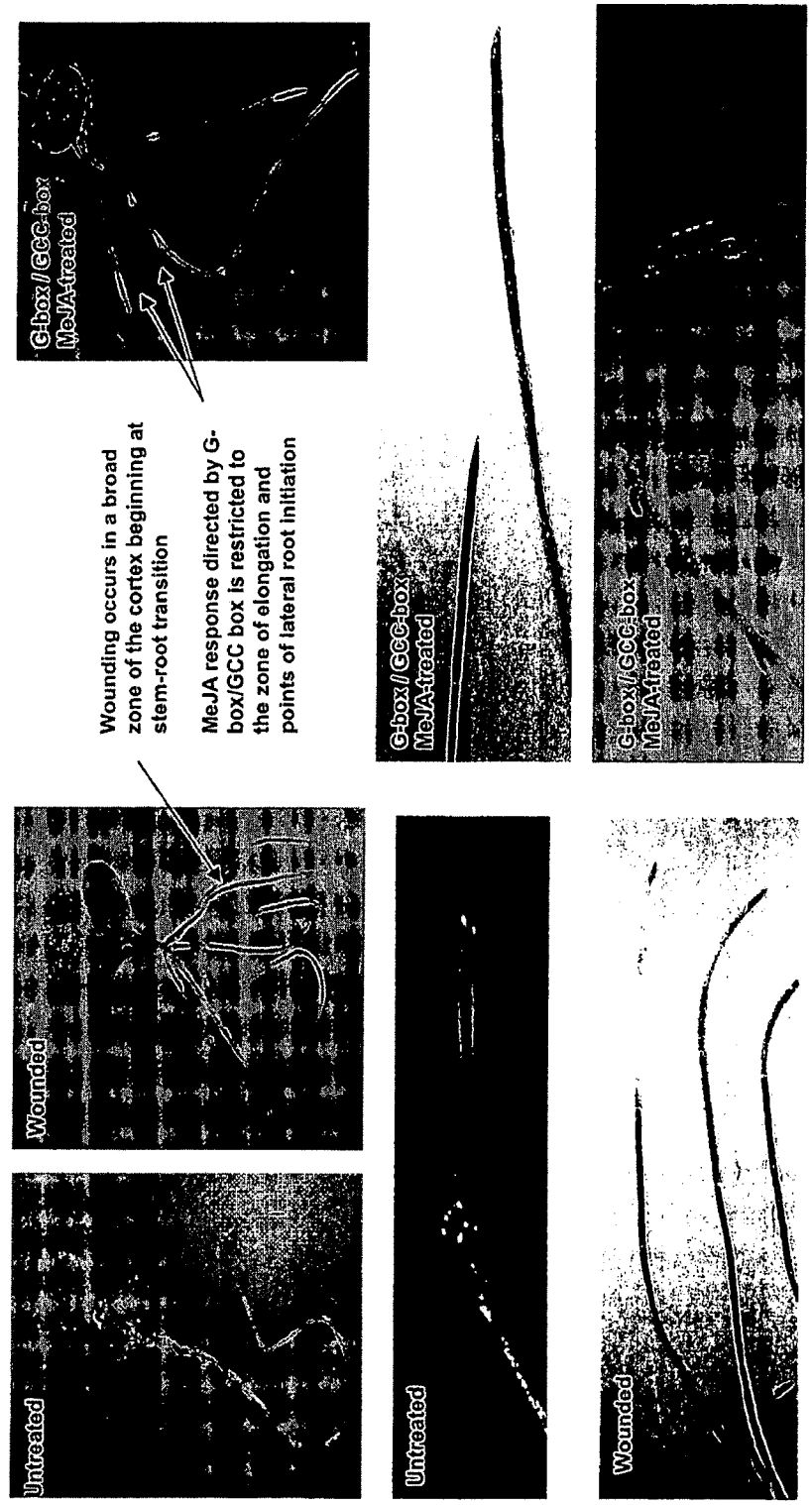
FIG. 7 shows MeJA inducibility of the G box-GCC construct and the GAG construct in transgenic tobacco plants as determined by histological analysis. Various portions of the transgenic plants were histochemically stained for GUS activity 48 hours after treatment with 100 μM MeJA. Plants not exposed to MeJA were also stained for GUS activity as negative controls. Blue color indicates promoter activity, and is only observed in plants containing the G box-GCC unit or the GAG motif, that have been either exposed to MeJA or subjected to wounding. Wounding response was observed in a broad zone of the cortex beginning at stem-root transition. MeJA response directed by the G box-GCC unit was observed in the zone of elongation and points of lateral root initiation.

Wounding and MeJA-Inducible Expression in Tobacco Roots Directed by the GAG and G Box-GCC Although a small number of jasmonate response elements have been characterized using cell cultures or transient expression systems, very few have been shown to be active in plants. The activities of the GAG motif and the G box-GCC unit in tobacco plants were evaluated. Transgenic plants were produced that contained the same tetramer constructs that were active in BY-2 cells. Several independent lines for each construct were tested for expression in untreated plants, wounded plants and MeJA-treated plants. FIG. 7 shows that both the GAG motif and the G box-GCC unit can direct wound-inducible expression and MeJA-inducible expression in the roots of tobacco plants. Untreated plants show a level of expression from both the GAG motif and the G box-GCC unit. This expression is restricted to the roots and can be typically found in the middle portions of the root away from the root apical meristem, root cap, and zone of elongation. Wounding of either the roots directly, or wounding of the leaves, led to up-regulation in expression from both promoter constructs but no change in the pattern of expression. The synthesis of nicotine alkaloids is induced in the roots of tobacco species after an insect attack, wounding, and jasmonate exposure. The inducibility of the GAG motif and the G box-GCC unit in roots as a result of wounding in the leaves indicates that by manipulating plants (e.g., insect attack, wounding, or topping) by physical means or by exposure to phytohormones, activation of PMT promoter activation mediated by the GAG motif can be useful for genetically controlling alkaloid biosynthesis pathway to produce higher or lower levels of nicotine and other alkaloids.

Plants were treated with 25 μM MeJA and stained after 72 hours to detect promoter activity. The GAG motif and the G box-GCC unit showed inducibility by MeJA, and displayed a remarkable change in expression pattern. Expression after 72 hours was still confined to the roots but shifted from the central and upper parts of the roots to an area nearer the root tip that appears to be associated with the elongation zone (FIG. 7). In addition, expression was also observed in areas around lateral root initials (FIG. 7). These results show that the GAG motif directs tissue-specific, wound-inducible expression, and Me-JA inducible expression. FIG. 7 also shows that only the 29 bp fragment ("G box-GCC unit") is required to direct this expression pattern. The wound-inducibility and MeJA-inducibility of the G box-GCC unit can be useful for genetically modifying nicotine biosynthesis by serving as a switch mechanism.

It will be appreciated that, although specific embodiments of the invention have been described herein for purposes of illustration, various modifications may be made without departing from the spirit and scope of the invention. Accordingly, the invention is not limited except as by the appended claims.

---

We claim:

1. A plant comprising an expression vector comprising four copies of a tripartite G-box like element/AT-rich element/GCC-like box element (GAG) motif operably linked to a heterologous promoter, wherein the G-box like element comprises the nucleic acid sequence of SEQ ID NO: 8, wherein the AT-rich element comprises the nucleic acid sequence of SEQ ID NO: 11, wherein the GCC-like box element comprises the nucleic acid sequence of SEQ ID NO: 7, wherein the four copies of the tripartite GAG motif are capable of inducing the heterologous promoter in the presence of methyl jasmonate, and wherein the promoter is operably linked to (a) a polynucleotide encoding a polypeptide or (b) a polynucleotide encoding an inhibitory nucleic acid molecule.

2. The plant of claim 1, wherein the plant is a transgenic tobacco plant.

3. The plant of claim 1, wherein the plant is a *Nicotiana tabacum* plant.

4. The plant of claim 1, wherein the polynucleotide sequence encodes a polypeptide.

5. The plant of claim 1, wherein the polynucleotide sequence encodes a molecule capable of suppressing the expression level of one or more genes involved in a biosynthetic pathway for the production of an alkaloid or nicotine.

6. The plant of claim 1, wherein the polynucleotide sequence encodes a protein involved in a biosynthetic pathway for the production of an alkaloid or nicotine.

7. A tobacco product comprising tobacco leaf from the *Nicotiana tabacum* plant of claim 3.

8. The tobacco product of claim 7, wherein the tobacco product is selected from the group consisting of a pipe, a cigar, a cigarette, chewing tobacco, leaf tobacco, shredded tobacco, and cut tobacco.

9. The plant of claim 1, wherein the polynucleotide sequence encodes an inhibitory nucleic acid molecule.

* * * * *

SEQUENCE LISTING

<160> NUMBER OF SEQ ID NOS: 24

<210> SEQ ID NO 1
<211> LENGTH: 74
<212> TYPE: DNA
<213> ORGANISM: Nicotiana tabacum

<400> SEQUENCE: 1
ctaaccctgc acgttgtaat gaatttttaa ctattatatt atatcgagtt gcgccctcca      60
ctcctcggtg tcca      74

<210> SEQ ID NO 2
<211> LENGTH: 8
<212> TYPE: DNA
<213> ORGANISM: Nicotiana tabacum

<400> SEQUENCE: 2 gcacgttg      8

<210> SEQ ID NO 3
<211> LENGTH: 28
<212> TYPE: DNA
<213> ORGANISM: Nicotiana tabacum

<400> SEQUENCE: 3
taatgaattt ttaactatta tattatat      28

<210> SEQ ID NO 4
<211> LENGTH: 25
<212> TYPE: DNA
<213> ORGANISM: Nicotiana tabacum

<400> SEQUENCE: 4
tgcgccctcc actcctcggt gtcca                                    25

<210> SEQ ID NO 5
<211> LENGTH: 47
<212> TYPE: DNA
<213> ORGANISM: Nicotiana tabacum

<400> SEQUENCE: 5
ctaaccctgc acgttgtcga gttgcgccct ccactcctcg gtgtcca             47

<210> SEQ ID NO 6
<211> LENGTH: 19
<212> TYPE: DNA
<213> ORGANISM: Nicotiana tabacum

<400> SEQUENCE: 6
cgagttccgc cctccactc                                           19

<210> SEQ ID NO 7
<211> LENGTH: 19
<212> TYPE: DNA
<213> ORGANISM: Nicotiana tabacum

<400> SEQUENCE: 7
cgagttgcgc cctccactc                                           19

<210> SEQ ID NO 8
<211> LENGTH: 10
<212> TYPE: DNA
<213> ORGANISM: Nicotiana tabacum

<400> SEQUENCE: 8
ctgcacgttg                                                     10

<210> SEQ ID NO 9
<211> LENGTH: 273
<212> TYPE: DNA
<213> ORGANISM: Nicotiana tabacum

<400> SEQUENCE: 9
ggagagagaa atgagcacac acatatacta acaaaattt actaataatt gcaccgagac    60
aaacttatat tttagttcca aaatgtcagt ctaaccctgc acgttgtaat gaattttaa   120 ctattatatt atatcgagtt gcgccctcca ctcctcggtg tccaaattgt atttaaatgc  180
atagatgttt attgggagtg tacagcaagc tttcggaaaa tacaaaccat aatactttct  240
cttcttcaat ttgtttagtt taattttgaa atg                             273

<210> SEQ ID NO 10
<211> LENGTH: 10
<212> TYPE: DNA
<213> ORGANISM: Nicotiana tabacum

<400> SEQUENCE: 10
ctgcttaatg                                                     10

<210> SEQ ID NO 11
<211> LENGTH: 28
<212> TYPE: DNA
<213> ORGANISM: Nicotiana tabacum

<400> SEQUENCE: 11
atatctaaaa taaagataat aaaatatt                                              28

<210> SEQ ID NO 12
<211> LENGTH: 19
<212> TYPE: DNA
<213> ORGANISM: Nicotiana tabacum

<400> SEQUENCE: 12
cgagttttaa tttccactc                                                        19

<210> SEQ ID NO 13
<211> LENGTH: 71
<212> TYPE: DNA
<213> ORGANISM: Nicotiana tabacum

<400> SEQUENCE: 13
ccaaccatgc acgttgtaat gattttttaa ctctattata tcgagttgcg ccctccactc           60
ctcggtgtcc a                                                                71

<210> SEQ ID NO 14
<211> LENGTH: 71
<212> TYPE: DNA
<213> ORGANISM: Nicotiana tabacum

<400> SEQUENCE: 14
ccaaccatgc acgttgtaat gattttttaa ctctattata tcgagttccg ccctccactc           60
ctcggtgtcc a                                                                71

<210> SEQ ID NO 15
<211> LENGTH: 71
<212> TYPE: DNA
<213> ORGANISM: Nicotiana tabacum

<400> SEQUENCE: 15
ccaaccatgc acgttgtaat gagttttaa ctctattatc tcgagttgcg ccctccactc            60
ctctgtgtcc a                                                                71

<210> SEQ ID NO 16
<211> LENGTH: 74
<212> TYPE: DNA
<213> ORGANISM: Nicotiana tabacum

<400> SEQUENCE: 16
ctaaccctgc acgttgtaat gaattttaa ctattatatt atatcgagtt gcgccctcca            60
ctcctcggtg tcca                                                             74

<210> SEQ ID NO 17
<211> LENGTH: 10
<212> TYPE: DNA
<213> ORGANISM: Nicotiana tabacum

<400> SEQUENCE: 17
atgcacgttg                                                                  10

```
<210> SEQ ID NO 18
<211> LENGTH: 57
<212> TYPE: DNA
<213> ORGANISM: Nicotiana tabacum

<400> SEQUENCE: 18
ctgcacgttg taatgaattt ttaactatta tattatatcg agttgcgccc tccactc      57

<210> SEQ ID NO 19
<211> LENGTH: 57
<212> TYPE: DNA
<213> ORGANISM: Nicotiana tabacum

<400> SEQUENCE: 19
ctgcttaatg atatctaaaa taaagataat aaaatattcg agttttaatt tccactc      57

<210> SEQ ID NO 20
<211> LENGTH: 29
<212> TYPE: DNA
<213> ORGANISM: Nicotiana tabacum

<400> SEQUENCE: 20
ctgcacgttg cgagttgcgc cctccactc                                      29

<210> SEQ ID NO 21
<211> LENGTH: 29
<212> TYPE: DNA
<213> ORGANISM: Nicotiana tabacum

<400> SEQUENCE: 21
ctgcttaatg cgagtttaa tttccactc                                       29

<210> SEQ ID NO 22
<211> LENGTH: 71
<212> TYPE: DNA
<213> ORGANISM: Nicotiana tabacum

<400> SEQUENCE: 22
ccaaccatgc acgttgtaat gatttttaa ctctattata tcgagttgcg ccctccactc    60
ctcggtgtcc a                                                         71

<210> SEQ ID NO 23
<211> LENGTH: 71
<212> TYPE: DNA
<213> ORGANISM: Nicotiana tabacum

<400> SEQUENCE: 23
ccaaccatgc acgttgtaat gatttttaa ctctattata tcgagttccg ccctccactc    60
ctcggtgtcc a                                                         71

<210> SEQ ID NO 24
<211> LENGTH: 71
<212> TYPE: DNA
<213> ORGANISM: Nicotiana tabacum

<400> SEQUENCE: 24
ccaaccatgt acgttgtaat gagttttaa ctctattatc tcgagttgcg ccctccactc    60
ctctgtgtcc a                                                         71
```